(12) United States Patent
Wright

(10) Patent No.: US 9,561,507 B2
(45) Date of Patent: Feb. 7, 2017

(54) DISPOSABLE THERMAL IN-VITRO DIAGNOSTIC APPARATUS

(71) Applicant: David W. Wright, Littleton, CO (US)

(72) Inventor: David W. Wright, Littleton, CO (US)

( * ) Notice: Subject to any disclaimer, the term of this patent is extended or adjusted under 35 U.S.C. 154(b) by 0 days.

(21) Appl. No.: 15/044,852

(22) Filed: Feb. 16, 2016

(65) Prior Publication Data

US 2016/0158760 A1 Jun. 9, 2016

Related U.S. Application Data

(62) Division of application No. 13/855,331, filed on Apr. 2, 2013, now Pat. No. 9,279,151.

(60) Provisional application No. 61/619,406, filed on Apr. 2, 2012.

(51) Int. Cl.
*B01L 7/00* (2006.01)
*C12Q 1/68* (2006.01)
*B01L 3/00* (2006.01)

(52) U.S. Cl.
CPC ................. *B01L 7/52* (2013.01); *B01L 3/508* (2013.01); *B01L 3/5027* (2013.01); *C12Q 1/686* (2013.01); *B01L 2200/147* (2013.01); *B01L 2200/16* (2013.01); *B01L 2300/044* (2013.01); *B01L 2300/048* (2013.01); *B01L 2300/0816* (2013.01); *B01L 2300/0887* (2013.01); *B01L 2300/12* (2013.01); *B01L 2300/165* (2013.01); *B01L 2300/1877* (2013.01); *B01L 2400/0633* (2013.01); *B01L 2400/0661* (2013.01); *B01L 2400/0683* (2013.01)

(58) Field of Classification Search
CPC ............ B01L 2200/147; B01L 2200/16; B01L 2300/044; B01L 2300/048; B01L 2300/0816; B01L 2300/0887; B01L 2300/12; B01L 2300/165; B01L 2300/1877; B01L 2400/0633; B01L 2400/0661; B01L 2400/0683; B01L 3/5027

See application file for complete search history.

(56) References Cited

U.S. PATENT DOCUMENTS 4,753,241 A 6/1988 Brannigan
2005/0129582 A1 6/2005 Breidford et al.

OTHER PUBLICATIONS

Wheeler et al., Anal. Chem. 2004, 76, 4011-4016.*
Emdtadmin., European medical Device technology, http://www.emdt.co.uk/article/microfluidics-platform-vitro-testing., pp. 1-2, Mar. 1, 2008.
Ahn et al., Proceedings of the IEEE, vol. 92, No. 1, pp. 154-170, Jan. 2004.

* cited by examiner

*Primary Examiner* — Cynthia B Wilder
(74) *Attorney, Agent, or Firm* — John D. Wright; Dickinson Wright PLLC

(57) ABSTRACT

A portable, disposable in-vitro diagnostic apparatus is provided. The apparatus includes a body configured to be hand held. The body has a reaction medium supply chamber configured in selective fluid communication with a reaction chamber via a fluid conveying channel. The reaction chamber is located beneath a sample reaction chamber. The reaction medium supply chamber contains a reaction fluid therein and the reaction chamber contains a thermal reaction medium therein. The reaction fluid is selectively reactive with the thermal reaction medium to produce one of an endothermic or exothermic reaction beneath the sample reaction chamber.

12 Claims, 13 Drawing Sheets

Bimetallic or thermally deformable disk with bias toward thermal conduction disk

DISPOSABLE THERMAL IN-VITRO DIAGNOSTIC APPARATUS

CROSS-REFERENCE TO RELATED APPLICATION

This application is a Divisional application of U.S. application Ser. No. 13/855,331, filed Apr. 2, 2013, which claims the benefit of U.S. Provisional Application Ser. No. 61/619,406, filed Apr. 2, 2012, all of which are incorporated herein by reference in their entirety.

BACKGROUND

1. Technical Field

This invention relates generally to in-vitro diagnostics, and more particularly to apparatus and methods for conducting thermally controlled in-vitro diagnostics.

2. Related Art

Biological diagnostic tests are a fundamental component in the process of determining the state or condition of a biological environment. These environments include, but are not limited to, human healthcare, agriculture, live stock management, municipal systems management, and national defense. Molecular tests that utilize nucleic acid detection provide an incredibly competitive level of specificity, sensitivity, and rapid timing from sampling to result. Nearly all nucleic acid detection approaches require signal amplification, such as Polymerase Chain Reaction (PCR), to generate detectable amounts of the targeted nucleic acid segment. Traditional mechanisms used in nucleic acid detection tests requiring PCR utilize high powered, immobile, non-disposable equipment to achieve large temperature gradients with high resolution. Although, these mechanism prove useful to obtain the test results desired, they are costly and are limited to use in fixed locations, given they require large, immobile equipment.

An assay is a sequence of steps or procedures used measure the presence or absence of a substance in a sample, the amount of a substance in a sample, or the characteristics of a sample. An example of a common point of care assay, or an assay conducted by a layperson is a blood glucose test. In this test, the blood is mixed with glucose oxidase, which reacts with the glucose in the sample, creating gluconic acid, gluconic acid in turn, reacts with a chemical in the assay called ferricyanide, producing ferrocyanide. Current is passed through the ferrocyanide and the impedance reflects the amount of glucose present.

Thermal cycling is a common method of accelerating a chemical reaction or promoting a biological event. Thermal cycling is a used to amplify segments of nucleic acid by via PCR. As shown in FIG. 1, in an example of a thermal cycling process, high temperature thermal cycling is used to physically separate two stands of a double helix DNA. This process is commonly referred to as denaturing, wherein the linked strands of the DNA are separated into two single strands. Temperatures maintained during denaturing are typically in the range of 94° to 96° C. The two separated strands from the denatured DNA are used as templates to logarithmically replicate identical copies of the targeted segment of DNA. Upon reducing the temperature to approximately 52° C., synthetically designed primers bind to, or "anneal" to the template DNA strands such that they flank both sides of a target segment of denatured strands of DNA. DNA Polymerase and other cofactors then cause the primer to extend fully along the denatured strands of DNA and thus, a new double stranded piece of DNA is generated, wherein a lower controlled temperature in the range of 70° to 80° C. is maintained.

The thermal cycling discussed above during denaturing and DNA replication is typically controlled in a laboratory machine. The machine includes electrical heating and cooling elements configured in electrical communication with thermal sensors in a closed loop control scheme. These machines are relatively large, immobile and expensive.

SUMMARY OF THE INVENTION

A portable, disposable, low-powered thermal cycling in-vitro diagnostic apparatus is provided in accordance with one aspect of the invention. The apparatus is economical and it provides a quick, reliable and economical method for performing a thermally activated in-vitro diagnostic test on a selected specimen, such as DNA, for example. Further, the apparatus automatically provides a predetermined thermal cycle over a predetermined time to allow a desired analysis of the specimen contained within the apparatus to be performed without need of human intervention. The apparatus produces exothermic and endothermic thermal energy, in a balanced and controlled environment via a chemical reaction between reactants contained within the apparatus. The reactants are provided and automatically combined in a predetermined manner to provide the desired thermal cycle needed to analyze the particular specimen. Accordingly, the apparatus in accordance with one aspect of the invention is wholly self-contained, and thus, is fully functional to perform the desired analysis without need of external apparatus.

In accordance with another aspect of the invention, the apparatus can be configured for operable attachment to an external source of power. The external source of power can be provided as a hand held device that is configured for attachment to the in-vitro diagnostic apparatus. The separate source of power can be re-used, while the apparatus remains disposable.

In accordance with another aspect of the invention, the external energy source can be configured to produce the desired energy profile within the apparatus. A simple circuit may provide for intermittent, or cycling of the energy source, resulting in a thermal cycling profile in the reaction chamber of the apparatus.

In accordance with another aspect of the invention, a portable, disposable in-vitro diagnostic apparatus includes a body configured to be hand held. The body has a reaction medium supply chamber configured in selective fluid communication with a reaction chamber via a fluid conveying channel. The reaction chamber is located beneath a sample reaction chamber. The reaction medium supply chamber contains a reaction fluid therein and the reaction chamber contains a thermal reaction medium therein. The reaction fluid is selectively reactive with the thermal reaction medium to produce one of an endothermic or exothermic reaction beneath the sample reaction chamber.

In accordance with another aspect of the invention, a conductive barrier separates the sample reaction chamber from the reaction chamber.

In accordance with another aspect of the invention, the portable, disposable in-vitro diagnostic apparatus includes an overflow chamber downstream from the reaction chamber.

In accordance with another aspect of the invention, a rupturable membrane selectively closes off the fluid conveying channel from the reaction medium supply chamber.

In accordance with another aspect of the invention, a self-actuatable valve is disposed between the fluid conveying channel and the reaction chamber. The self-actuatable valve is movable between a closed position to close off the fluid conveying channel from the reaction chamber and an open position to allow fluid to flow from the fluid conveying channel into the reaction chamber.

In accordance with another aspect of the invention, a method of conducting an in-vitro diagnostic test is provided. The method includes providing a body configured to be hand held having a reaction medium supply chamber with a reaction fluid contained therein in selective fluid communication with a thermal reaction medium contained in a reaction chamber via a fluid conveying channel wherein the reaction chamber is beneath a sample reaction chamber; disposing a sample in the sample reaction chamber; and dispensing a reaction fluid from the reaction medium supply chamber into the reaction chamber and producing one of an endothermic or exothermic reaction within the reaction chamber beneath the sample reaction chamber.

In accordance with another aspect of the invention, the method further includes depressing a bulb and causing the reaction fluid to rupture a membrane and flow into the reaction chamber.

In accordance with another aspect of the invention, the method further includes causing a self-actuable valve to move between open and closed positions to respectively allow and prevent the flow of the reaction fluid into the reaction chamber in response to the endothermic or exothermic reaction.

In accordance with another aspect of the invention, the method further includes causing the self-actuable valve to move between the open and closed positions by buffering a portion of the thermal reaction medium.

In accordance with another aspect of the invention, the method further includes reacting water with CuSO4 to produce an exothermic reaction.

In accordance with another aspect of the invention, the method further includes reacting oxygen with iron to produce an exothermic reaction.

In accordance with another aspect of the invention, the method further includes reacting citric acid with sodium bicarbonate to produce an endothermic reaction.

BRIEF DESCRIPTION OF THE DRAWINGS

These and other aspects, features and advantages of the invention will become more readily appreciated when considered in connection with the following detailed description of presently preferred embodiments and best mode, appended claims and accompanying drawings, in which:

DETAILED DESCRIPTION OF PRESENTLY PREFERRED EMBODIMENTS

Figure 12A:
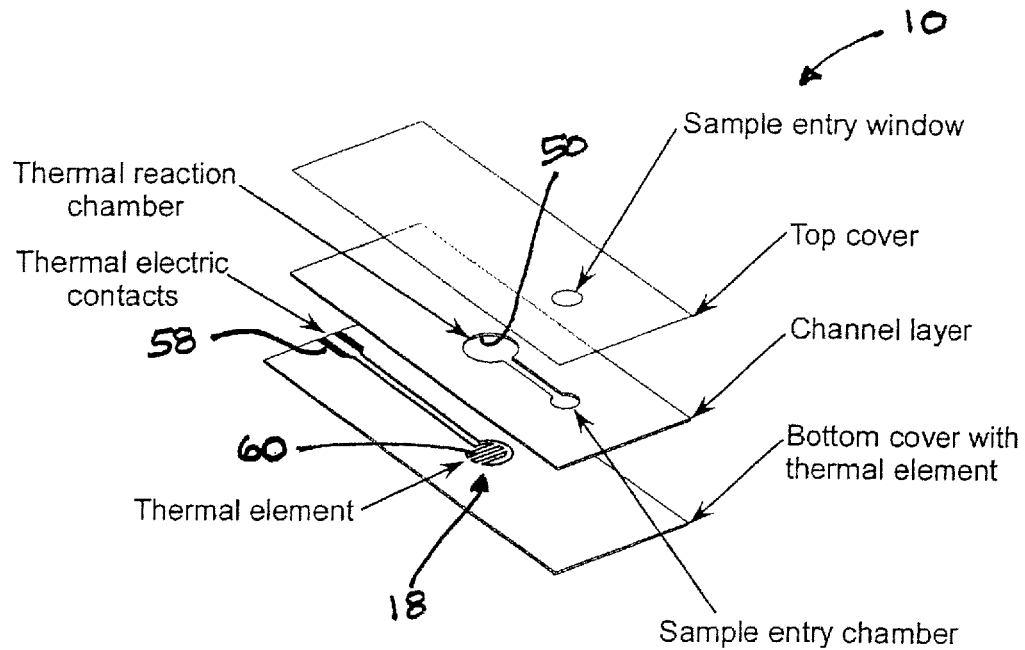
FIG. 12A illustrates an exploded perspective view of a disposable in-vitro diagnostic apparatus constructed in accordance with yet another aspect of the invention.
Figure 12B:
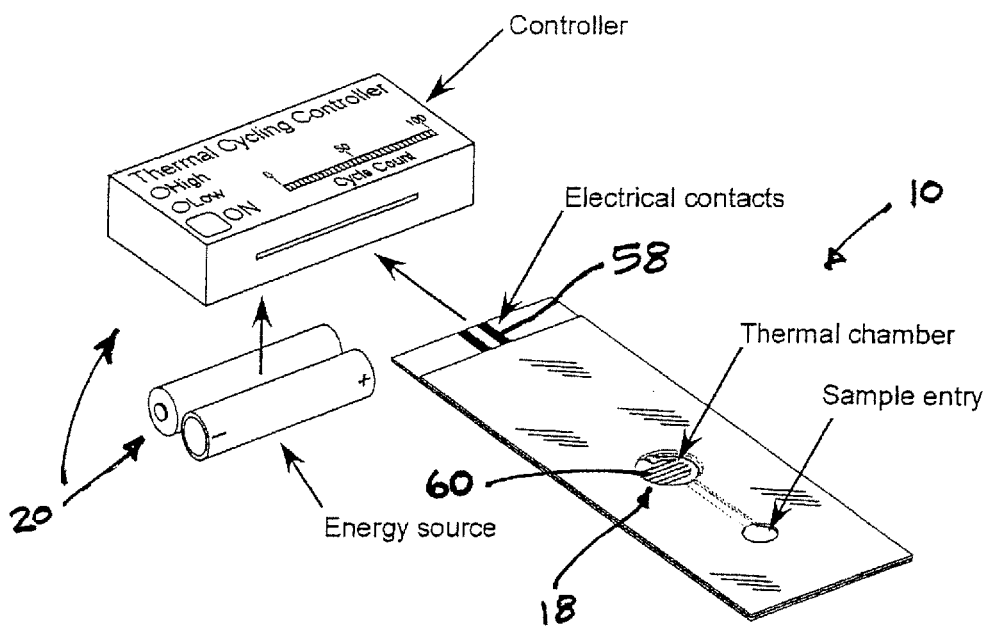
FIG. 12B illustrates the apparatus of FIG. 12A in combination with an external energy supply device.

Referring in more detail to the drawings, disposable in-vitro diagnostic apparatus, referred to hereafter as apparatus 10, constructed in accordance with various presently preferred embodiments of the invention are illustrated, by way of example and without limitation. The apparatus 10 provide a quick, reliable and economical method for performing a thermally activated in-vitro diagnostic test on a selected specimen. The apparatus 10 is both economical in manufacture and in use, is readily portable, such that it is sized to be hand held for single use, whereupon the apparatus 10 is disposable after use, particularly given the low cost associated with its manufacture. The apparatus 10 can be provided as an all inclusive device, including an integral exothermic reaction heat producing or endothermic heat reducing and regulating mechanism, or it can be configured for operable electrical connection to a separate energy source to power a thermal reaction within the apparatus (FIGS. 12A-12B). If configured for operable attachment to a separate energy source, the energy source and/or the apparatus 10 can be configured to regulate the thermodynamics within the apparatus 10, as discussed further below.

The heat production via the exothermic chemical reaction or heat reduction via the endothermic reaction may be achieved by combining two or more elements or chemical substances, known as reactants, provided and contained entirely and integrally within the apparatus 10. The combination of the reactants produces a product and a release of energy or a reduction of energy from the surrounding environment. The change in enthalpy, (thermodynamic potential) for an exothermic reaction is less than zero (<0), and thus, a larger value of energy released in the reaction is subtracted from a smaller value of energy used to initiate the reaction, the opposite being true for an endothermic reaction.

The exothermic reactants may be provided individually as, or as a combination of, solids, liquids and gasses. Some examples include:

Combining anhydrous copper (II) sulfate with water (Solid+Liquid):

$CuSO_4 + 5H_2O \rightarrow CuSO_4 \cdot 5H_2O + HEAT$; or

Combining oxygen with iron (Gas+Liquid):

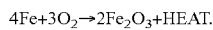

$4Fe + 3O_2 \rightarrow 2Fe_2O_3 + HEAT$.

The endothermic reactants may be provided individually as, or as a combination of, solids, liquids and gasses. Some examples include:

Combining citric acid and sodium bicarbonate:

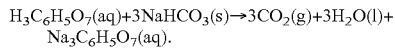

$H_3C_6H_5O_7(aq) + 3NaHCO_3(s) \rightarrow 3CO_2(g) + 3H_2O(l) + Na_3C_6H_5O_7(aq)$.

Figure 6:
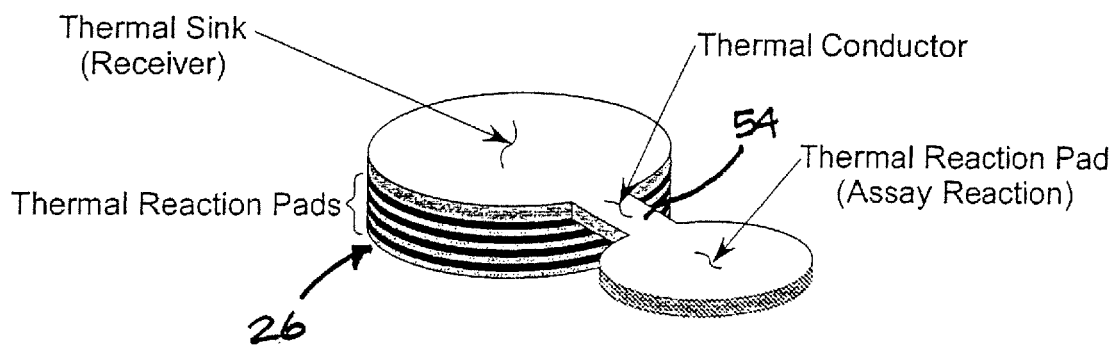
FIG. 6 is a perspective view of thermal transfer mechanism constructed in accordance with another aspect of the invention in combination with an exothermic or endothermic reaction member.

Additionally, as shown in FIG. 6, heat or cooling can be generated remotely from the sample being heated or cooled. Remote transport of thermal energy is provided by conduction through a material of high thermal conductivity, expressed in units of power per distance multiplied by temperature; W/m·K or W/m °C., Btu/(hr °F. ft²/ft). Remote heat transfer provides distribution of the thermal energy throughout the disposable device to locations desired, and also provides a source of varying temperature gradient to one or more points.

In accordance with one aspect of the invention, as shown in FIGS. 7-9, the apparatus 10 can include a thermal cycling mechanism 12 to regulate and vary the heat or subtraction of energy transferred to or from to the sample. The thermal cycling mechanism 12 can be configured via a multi-layered composite, producing a thermal cycle based on the rate of reaction, quantity of reactants present and desired thermal cycling frequency. As the exothermal or endothermal reaction progresses, the heat or cooling produced by the chemical reaction may be regulated by the thermal regulating mechanism 12, which can include a valve member 13, such as a bimetallic member, located between the thermal source and the sample being heated or cooled. The bimetallic member 13 is designed to move between an actuated and non-actuated position at predetermined temperatures, thus, providing an automated temperature regulation and a thermal cycling profile. This function can be applied to the above described remote thermal transport element (FIG. 6) and to an electrical thermal energy control by acting as an electric switch (FIGS. 12 and 13).

Figure 9A:
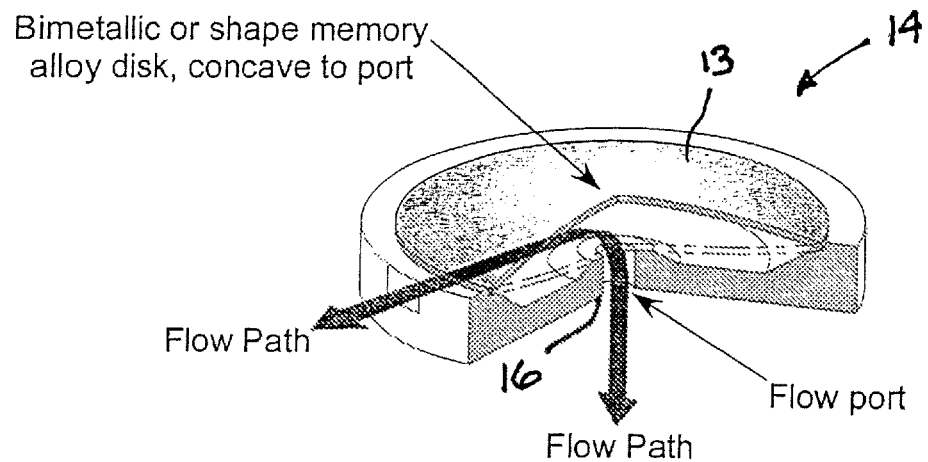
FIGS. 9A-9C illustrate a valve for regulating the flow of a reactant in a disposable in-vitro diagnostic apparatus constructed in accordance with another aspect of the invention.
Figure 9B:
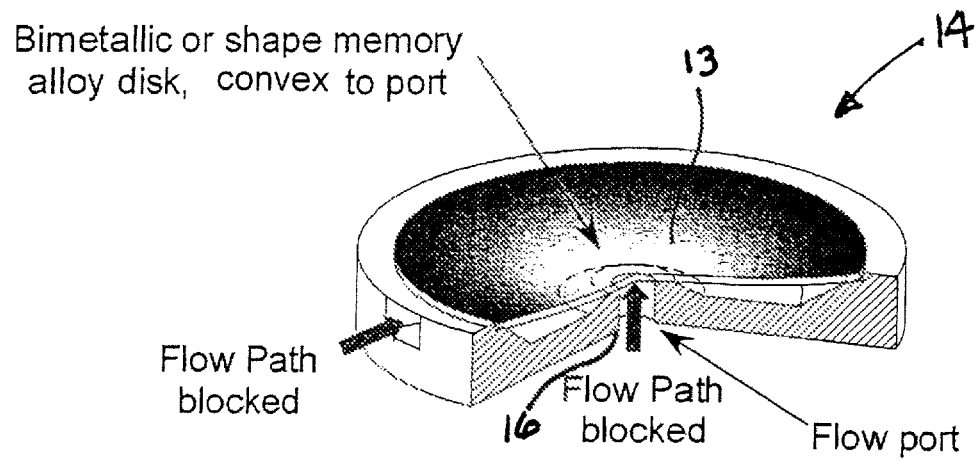
Figure 9C:
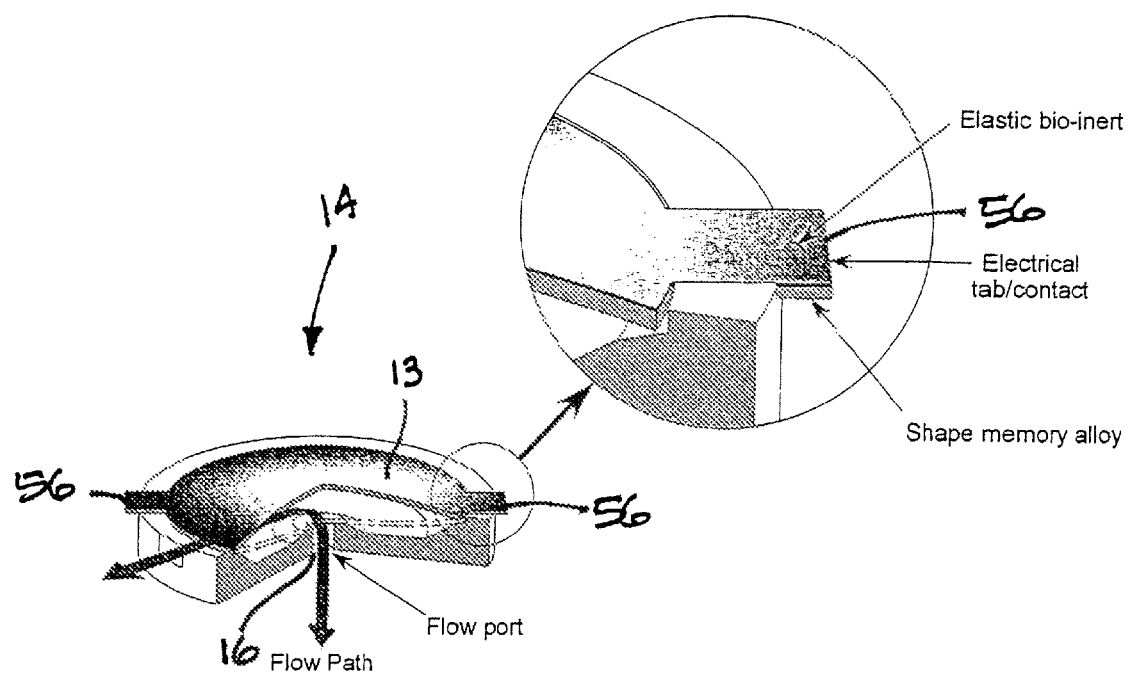

As shown in FIGS. 9A-9C, thermal cycling within the apparatus 10 can be provided via a bimetallic, thermally actuated valve 14, which, at a predetermined temperature, changes from concave (FIG. 9A) to convex (FIG. 9B) with respect to a valve port 16. Upon heating or cooling to the predetermined actuation temperature, the valve 14 moves to a closed convex configuration (FIG. 9B), thus closing off flow of the reactant through the valve port 16, and upon cooling the valve 14 moves to an open concave configuration (FIGS. 9A and 9C), thus restoring the flow of the reactant through the valve port 16. The mechanical threshold of actuation results in a "snapping action" upon the valve member 13 "crossing over center".

As shown in FIGS. 12A-13B, in addition to, or in lieu of producing heat via a chemical reaction mechanism within the apparatus 10, heat may be generated by placement of an electrical heating element 18 proximal to the sample being heated. The heating element 18 may be actuated by an energy source 20, such as a DC battery, by way of example, located integrally within the disposable apparatus 10 (FIG. 13A-13B), or from a separate energy source 20 external to the apparatus 10, such as a DC battery, by way of example, which is configured to interface electrically with the disposable device (FIGS. 12A-12B).

An electrical switch can be provided by a manual switch or by a low-level resistive or capacitance switch via contact with the sample fluid and coupled with a transistor on the apparatus 10. Furthermore, a temperature reactive bimetallic switch may be employed, proximal to the fluid sample, such as discussed with regard to FIGS. 7A-7C, to regulate the temperature, or to produce a thermal cycling profile.

Figure 11A:
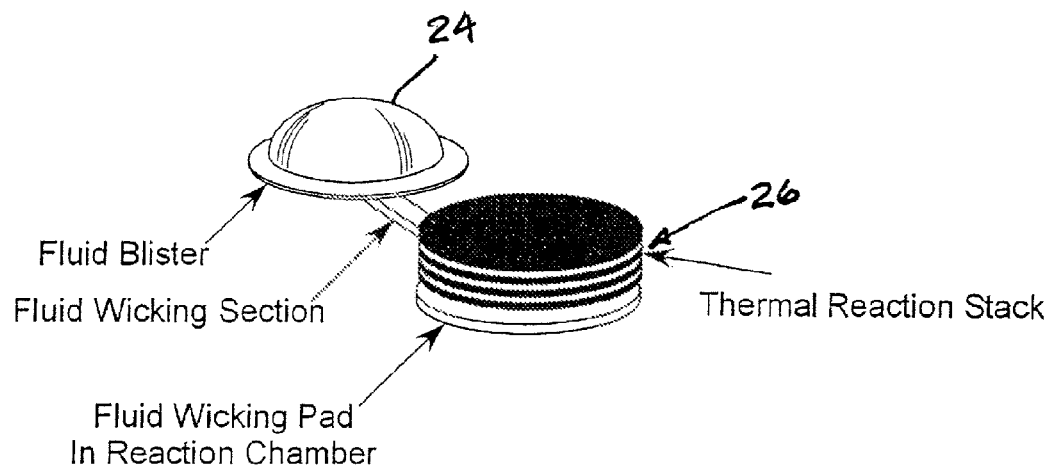
FIG. 11A illustrates a perspective view of a fluid activation system of a disposable in-vitro diagnostic apparatus constructed in accordance with another aspect of the invention.
Figure 11B:
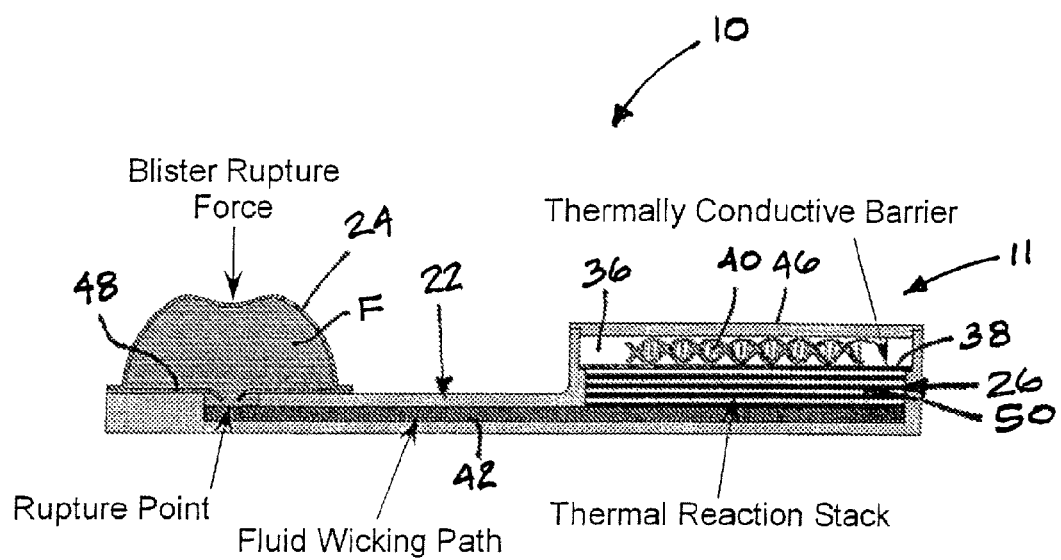
FIG. 11B is a cross-sectional plan view of the apparatus of claim 11A.

As shown in FIGS. 11A-11B, the fluid reactant channeled to promote the thermal reaction may be introduced to the reaction chamber by a wick member 22, and/or a controlled capillary channel. This mechanism and method of channeling the reactant can be configured to regulate the rate of fluid transfer as desired, thereby allowing the heat or cooling generated to be controlled, as desired. One or more fluid blisters 24 containing the fluid reactant F, or other sources of reactant, are provided to initiate the thermal reaction cycle. Additionally, fluid reactants having different reactivity can be provided via the different sources of reactant, which provide a mechanism and method for varying thermal profiles. The sequential introduction of the fluid reactants at prescribed time intervals further facilitate regulating the thermal profile and timing thereof.

Figure 1:
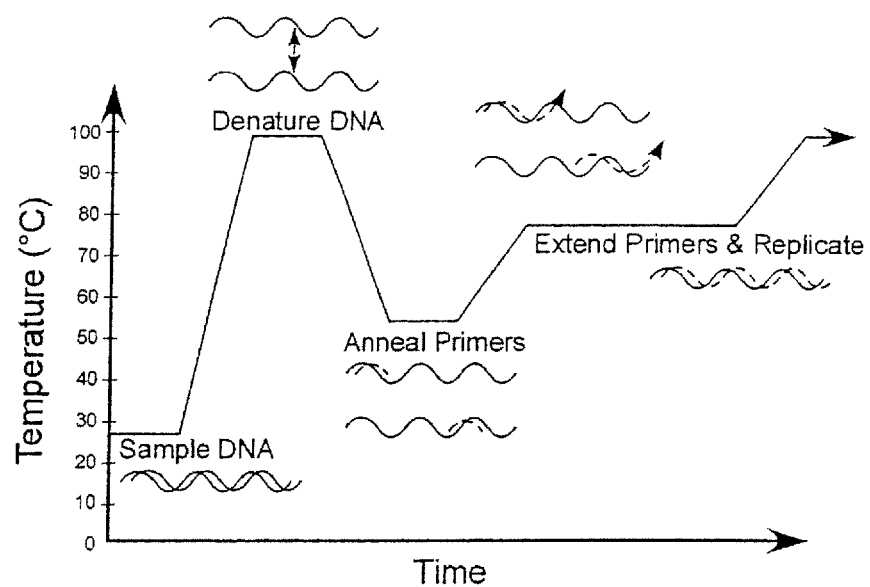
FIG. 1 illustrates an example of a typical thermal cycle profile used in a denaturing and replication process of DNA.
Figure 2:
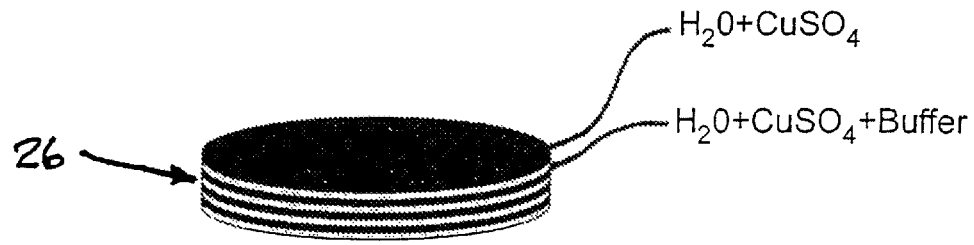
FIG. 2 illustrates a perspective view of an exothermic or endothermic reaction member constructed in accordance with one aspect of the invention.

In FIG. 2, an exothermic multi-layered composite medium, shown as a disk stack 26 of alternating exothermic values, is illustrated in accordance with one aspect of the invention. As the reaction progresses, the quantitative level of exothermic energy produced alternates in accordance to the desired thermal output level, thus, achieving the desired thermal cycle. The outer peripheral sides of the stack 26 can be shielded from the chemical reactant, such as by an inert coating, not subject to dissolution upon exposure to the reactive fluid. The exothermal reactant chemical discussed above, CuSO4 is provided as an example, and thus, it should be recognized that additional endothermic and exothermic reactive solids could be used.

Figure 3A:
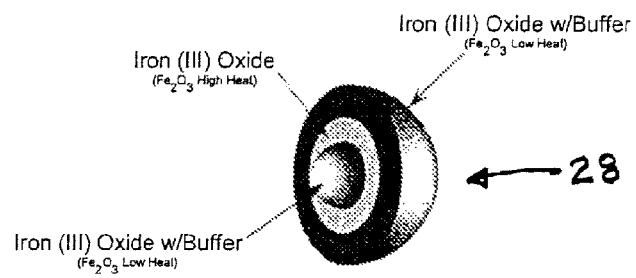
FIG. 3A illustrates a partial cross-sectional view of an exothermic or endothermic reaction member constructed in accordance with another aspect of the invention.

In FIG. 3A, an exothermal or endothermal composite medium, shown as a bead or sphere 28, is illustrated in accordance with another aspect of the invention, which is a derivation of the exothermic composite disk stack 26, with the primary difference of surface area and the number of individual points of reaction. A plurality of the composite spheres 28 provides an increased outer reactive surface area, and thus, provides a more intense reaction. The plurality of reactive spheres 28 can be provided in a predetermined configuration and quantity to produce the desired thermal cycling effect.

Figures 3B, 3C:
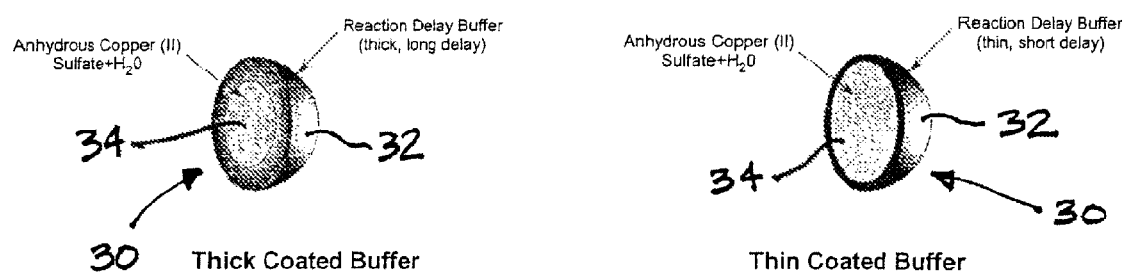
FIGS. 3B-3C illustrate cross-sectional views of an exothermic or endothermic reaction members constructed in accordance with further aspects of the invention.

In FIG. 3B-3C, exothermal or endothermal composite beads or spheres 30 are illustrated in accordance with another aspect of the invention. The exothermal or endothermal spheres 30 are similar to the previously discussed composite beads or spheres 28 of FIG. 3A, however, they are buffered with a coating 32. The buffered coating 32 provides a timed-release of the active agent 34 in the exothermic reaction. Reactive spheres 30 having differing buffers 32 and thicknesses of buffer 32 (FIG. 3B being thicker than FIG. 3C) result in a staged thermal cycle, as desired. A further difference with the buffered exothermal or endothermal composite spheres 30 over the spheres 28 of FIG. 3A is that the buffered spheres 30 of FIGS. 3B-3C each consist of only one reactive element 34 internal to the buffered coating 32.

Figure 4A:
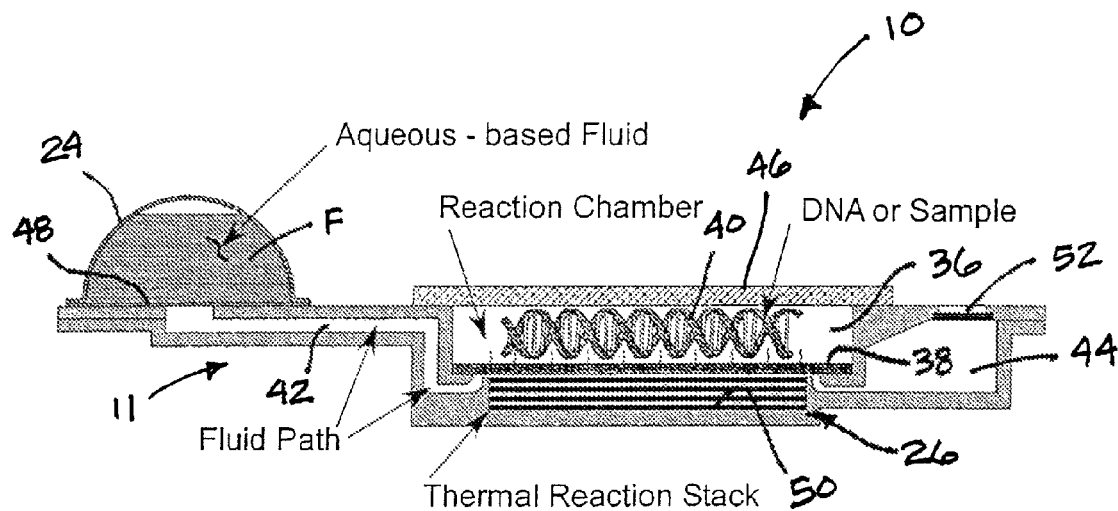
FIGS. 4A-4B illustrate respective cross-sectional plan and perspective views of a deactivated disposable in-vitro diagnostic apparatus constructed in accordance with one aspect of the invention utilizing an exothermic or endothermic reaction member of FIG. 2.
Figure 4B:
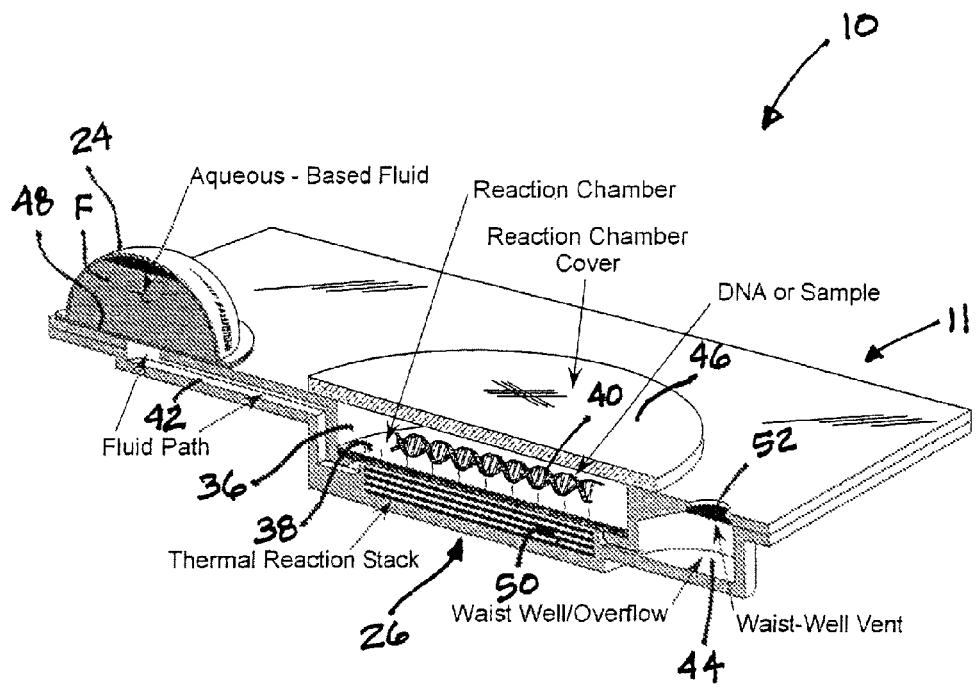

In FIGS. 4A-4B, an apparatus 10, constructed in accordance with one aspect of the invention, includes a unitized housing or body 11 sized to be hand held, and thus, the body 11 is readily carried in a palm of a hand. The body 11 can be constructed of any suitable materials, preferably relatively inexpensive moldable polymeric materials. The body 11 carries and provides the components of the apparatus 10 as a unitized, portable and disposable assembly. In accordance with one aspect of the invention, the body 11 carries an exothermal or endothermal composite series of plates or disks 26, also referred to as a "reaction" stack, such as discussed and shown in FIG. 2, residing under a sample reaction chamber 36. The chamber 36 is separated from the thermal reaction stack 26 by a thermally conductive barrier 38, thus isolating the byproducts of the thermal reaction from the sample 40 being heated or cooled. A self-contained reactive fluid F is encapsulated and contained in a flexible and sealed elastic bulb or blister, also referred to as a reaction fluid supply chamber 24, shown as a "blister pack", that is in selective fluid communication with the thermal reaction medium or stack 26 contained in a reaction chamber 50 via a fluid conveying channel 42, and to a distal (downstream of the sample 40) waste/overflow chamber 44, which is vented to atmosphere or another chamber. The sample chamber 36 may be covered and seal off by an optically clear cover window 46 to permit visual or optical analysis of the reaction within the chamber 36.

Figure 5A:
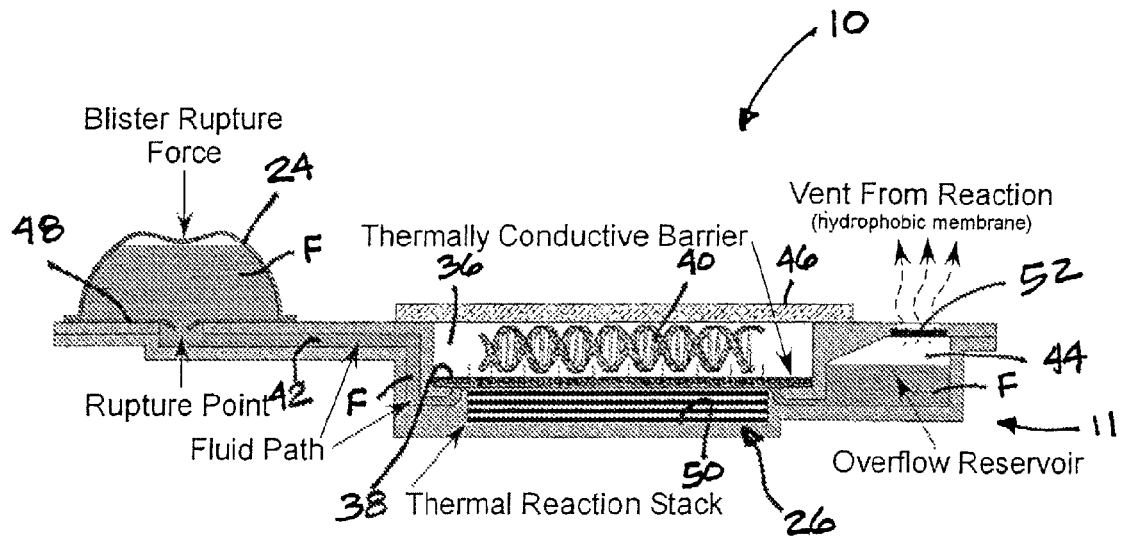
FIG. 5A illustrates the apparatus of FIGS. 4A-4B in an activated state.
Figure 5B:
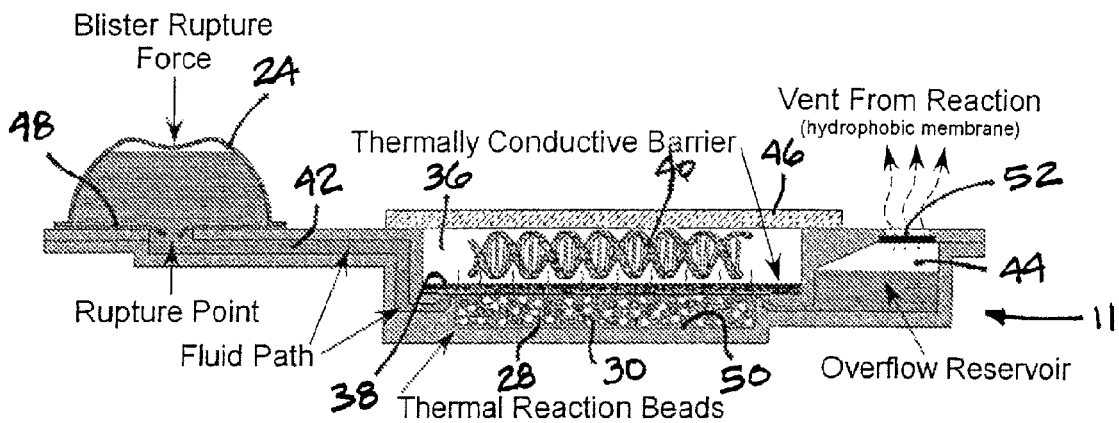
FIG. 5B is a view similar to FIG. 5A illustrating a disposable in-vitro diagnostic apparatus constructed in accordance with another aspect of the invention utilizing exothermic or endothermic reaction members of at least one of FIGS. 3A-3C.

As best shown in FIGS. 5A-5B, the blister 24 containing the reactive fluid F is depressed via an externally applied force, such as by manually depressing the blister 24 with a thumb or finger, for example, thereby causing the reactive fluid to selectively rupture a membrane 48 closing off the channel 42. Upon the membrane 48 being ruptured, the fluid passes through the channel 42 to the reaction chamber 50 containing the thermal reaction stack 26. The stack 26 reacts with the reactive fluid F, thereby producing an endothermic or exothermic release of energy. The thermally conductive barrier 38 conducts or removes the thermal energy to or from the sample 40 being heated or cooled. Excess fluid travels to the waste/overflow chamber 44, and the gases produced by the reaction are vented via a hydrophobic membrane 52, thus balancing the pressures present within the disposable apparatus 10. FIG. 5B is similar to FIG. 5A, however, it incorporates at least one or more types of the exothermal or endothermal reactive beads or spheres 28, 30 discussed above and shown in FIGS. 3A-3C. As with FIG. 5A, the reaction is vented, thus balancing the pressures present within the disposable apparatus 10.

FIG. 6 depicts the use of a thermal conductor 54 to transfer the thermal energy to or from the point of an assay reaction. This allows remote generation of energy, thus, multiple sources of energy may be directed to a single point or location. The figure discussed above represent only a single location of energy.

Figure 7A:
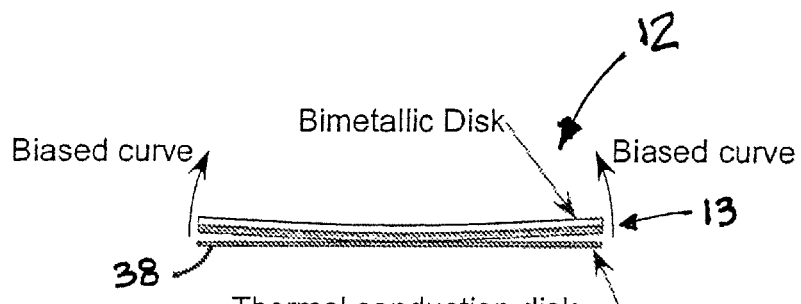
FIGS. 7A-7C illustrate various states of a thermal control mechanism constructed in accordance with another aspect of the invention for regulating the thermal energy in an apparatus constructed in accordance with another aspect of the invention.
Figure 7B:
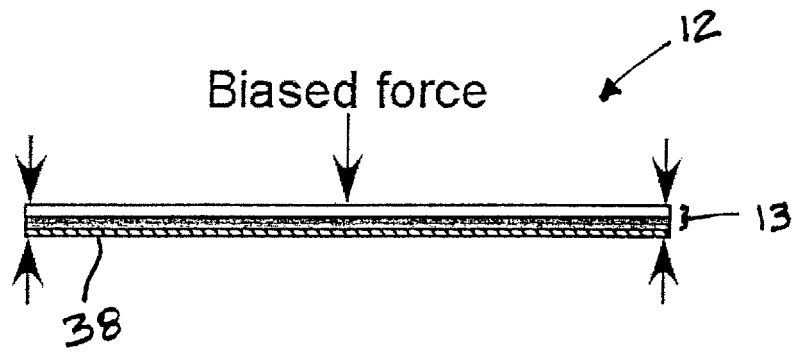

FIG. 7A depicts the thermally cycling mechanism in the form of a deformable bimetallic or shape memory alloy disk 12. The objective of this component is to regulate the level of thermal energy extended to or from the assay chamber 36. The thermal barriers 38 shown in FIGS. 4A-4B and 5A-5B can be provided as such, such as via a bimetallic, shape memory alloy or other thermally deformable material, thus allowing for the thermal barrier 12 to automatically change its configuration at a prescribed temperature. The deformable thermal barrier 12 is in contact with the thermally conductive member 38 prior to the thermal reaction. The bias shape of FIG. 7B provides positive physical abutment of the thermal barrier 12 with the thermally conductive member 38 upon assembly of the thermal barrier 12 and prior to heating or cooling. It should be recognized that the thermal barrier 12 can be constructed having any desired shape.

Figure 7C:
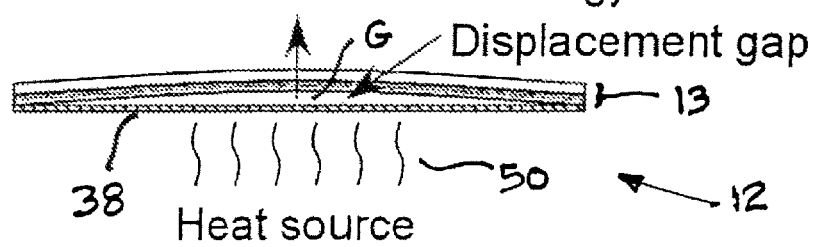

FIG. 7C depicts the thermally deformable, or shape memory alloy barrier 12, deflected at a prescribed temperature, lifting off of the thermally conductive member 38, thus limiting the conduction of energy from the thermal reaction chamber 50 via an insulation gap G. The natural resonate frequency governing the period between deflection and non-deflection is a function of design and temperature. This frequency results in the desired thermal cycling between the configurations shown in FIGS. 7B and 7C.

Figure 8A:
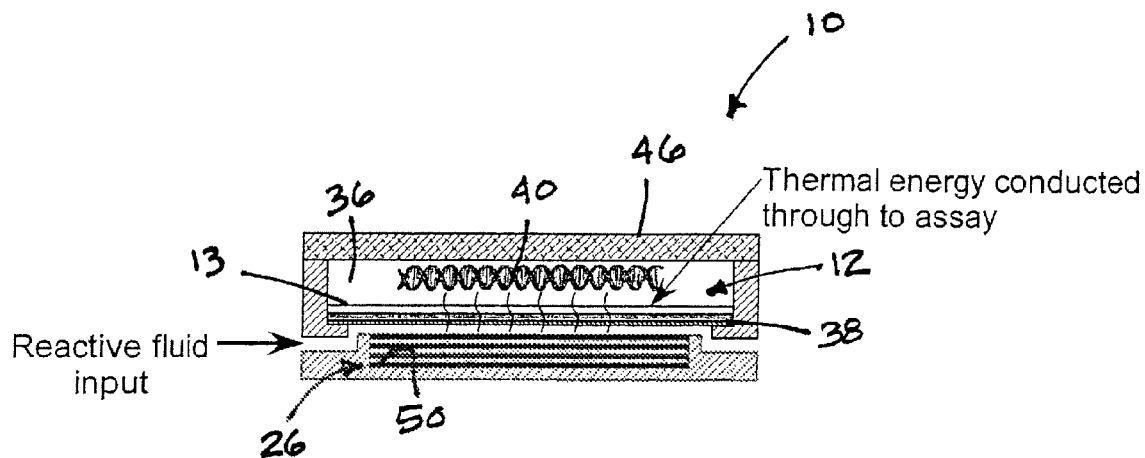
FIG. 8A illustrates a portion of a disposable in-vitro diagnostic apparatus constructed in accordance with the invention incorporating the thermal control mechanism of FIGS. 7A-7C with the thermal control mechanism shown in a maximum thermal energy conveying conduction state corresponding to FIG. 7B.

FIG. 8A illustrates an apparatus 10 including the thermally deformable barrier 12 of FIGS. 7A-7C, in the un-actuated state. While, in its un-actuated state, thermal energy resulting from a combination of the fluid reactant F and the exothermal or endothermal composite medium is conducted through the thermally conductive barrier 38 and through the thermally deformable barrier 12.

Figure 8B:
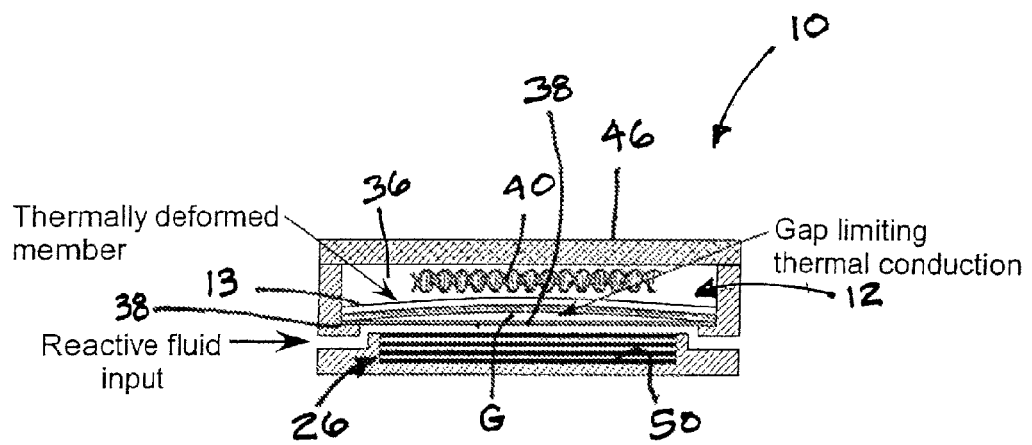
FIG. 8B shows the apparatus of FIG. 8A with the thermal control mechanism shown in a minimum thermal energy conveying convection state corresponding to FIG. 7C.

FIG. 8B depicts the thermally deformable barrier 12 deflected (actuated) at a prescribed temperature to provide the gap G, thus limiting the conduction of energy from the thermal reaction chamber 50 to the sample chamber 36. Upon reaching a designed target temperature, the thermally deformable barrier 12 looses physical conduct with the thermally conductive barrier 38, thus eliminating conduction of heat or cooling from the reaction chamber 50 to the sample chamber 36. The thermally deformed material 12 returns to its physically conductive position (FIG. 8A) upon cooling. The cooling process occurs due to the lack of physical contact with the heated or cooled conduction surface 38.

FIGS. 9A-9B depict the valve 14 comprised of a thermally deformable or shape memory alloy device 13, capable of deflecting at a prescribed temperature, thus regulating the flow of reaction fluid F to the reaction chamber 50. In FIG. 9A the valve 14 is shown in the open position, wherein the fluid F is able to flow to the reaction chamber 50. A thermal conductor 54, as described and shown in FIG. 6, may be adapted to this design to allow control of the valve 14 from a remote location. This valve 14 would also produce a thermal cycling, upon opening and closing, to regulate a thermal reaction.

FIG. 9B depicts the valve 14 in the closed position, thereby preventing the flow of the fluid reactant F to the reaction chamber 50. As such, the thermal reaction "downstream" of the valve 14 is impeded, thus reducing the thermal energy the valve 14 is exposed to, resulting in a reopening of the valve 14.

FIG. 9C depicts a thermally deformable shape memory valve 14 with electrical contacts 56 for electrical actuation. Nitinol, a common shape memory alloy undergoes elastic deformation upon thermal or electrical exposure. The valve 14 deflects upon passing current through the valve 14.

Figure 10A:
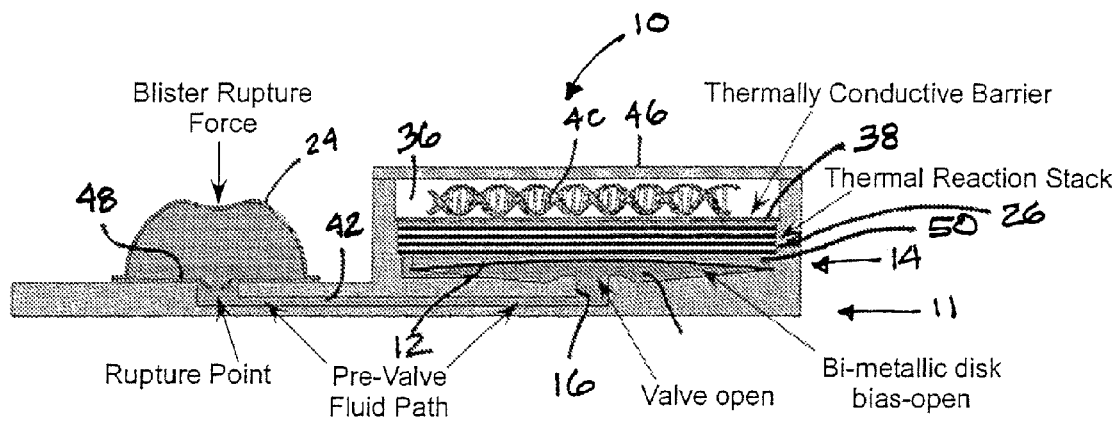
FIGS. 10A-10B illustrate a disposable in-vitro diagnostic apparatus incorporating the valve of FIGS. 9A-9B with the valve being shown in respective open and closed states.
Figure 10B:
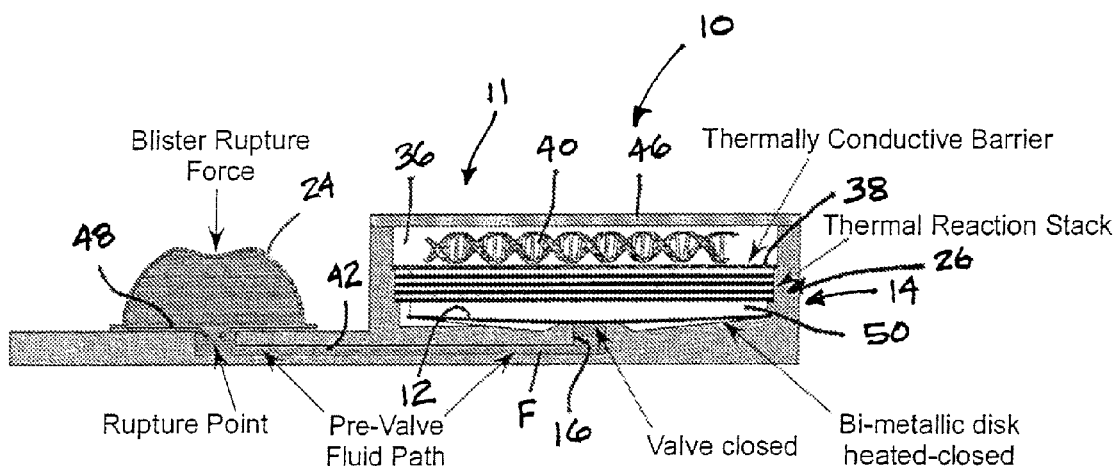

FIG. 10A illustrates an apparatus 10 incorporating the valve 14 in FIGS. 9A-9C, and also the thermally deformable member 12 described in FIGS. 7A-8B. The valve 14 is shown in the open position, permitting flow of the liquid reaction agent F to the solid reactant. FIG. 10B depicts the integrated thermal valve 14 in the closed position, thus inhibiting the flow of the liquid reaction agent into fluid contact with the solid reactant 26.

FIG. 11A depicts a device for introducing the reaction fluid into the reaction chamber remotely via the wick member 22. The wick 22 regulates the flow of the reaction fluid into the reaction chamber 50, thus regulating the rate of the reaction. The wick 22 can be provided having any desired cross-sectional shape along its length, and further, can be formed from any desired wicking material, thereby allowing the flow rate of wicking of the reaction fluid to be precisely controlled.

FIG. 11B is a cross-section of an apparatus 10 incorporating the remote fluid wicking device 22 of FIG. 11A.

FIG. 12A depicts a disposable apparatus 10 constructed in accordance with another aspect of the invention including the embedded thermal element 18 and electrical contacts 58 for interface with the electrical energy source 20. The thermal element 18 includes a resistive element 60 embedded in the reaction chamber 50. The external energy source 20 provides the current to heat the resistive elements 60.

FIG. 12B shows the apparatus 10 in FIG. 12A interfacing with an external energy source 20. The energy source 20 is capable of producing an energy profile, which in turn, produces the desired thermal profile. A simple circuit may provide for intermittent, or cycling of the energy source 20, resulting in a thermal cycling profile in the reaction chamber 50.

Figure 13A:
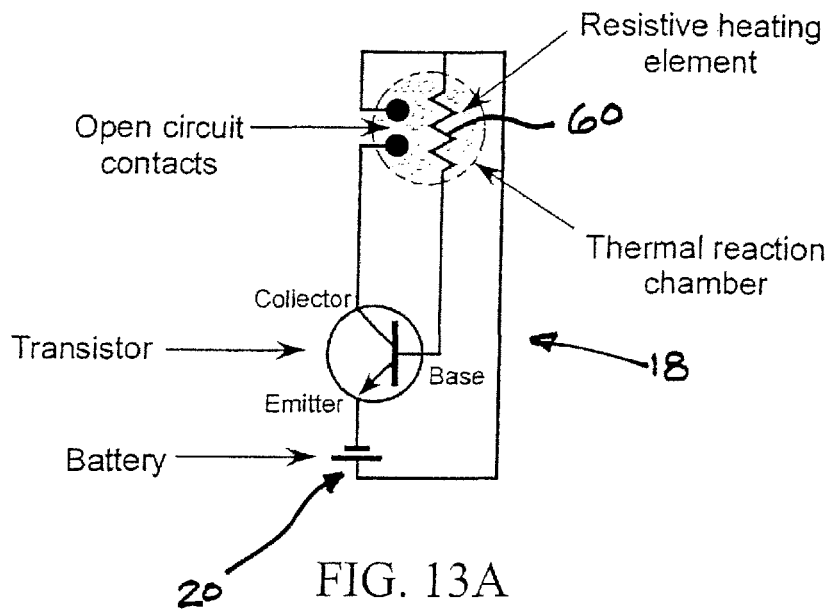
FIG. 13A is a schematic of energy supply device for use on a disposable in-vitro diagnostic apparatus constructed in accordance with another aspect of the invention.

FIG. 13A is a schematic of a "on-device", battery powered heating element, with a simple transistor relay. The transistor receives its signal from a pair of contacts embedded in the reaction chamber 50 which are "connected" upon contact with the fluid sample being heated. The fluid sample provides and electrical path between the contacts, thus completing the circuit. The addition of a thermal switch would provide a thermal cycling profile.

Figure 13B:
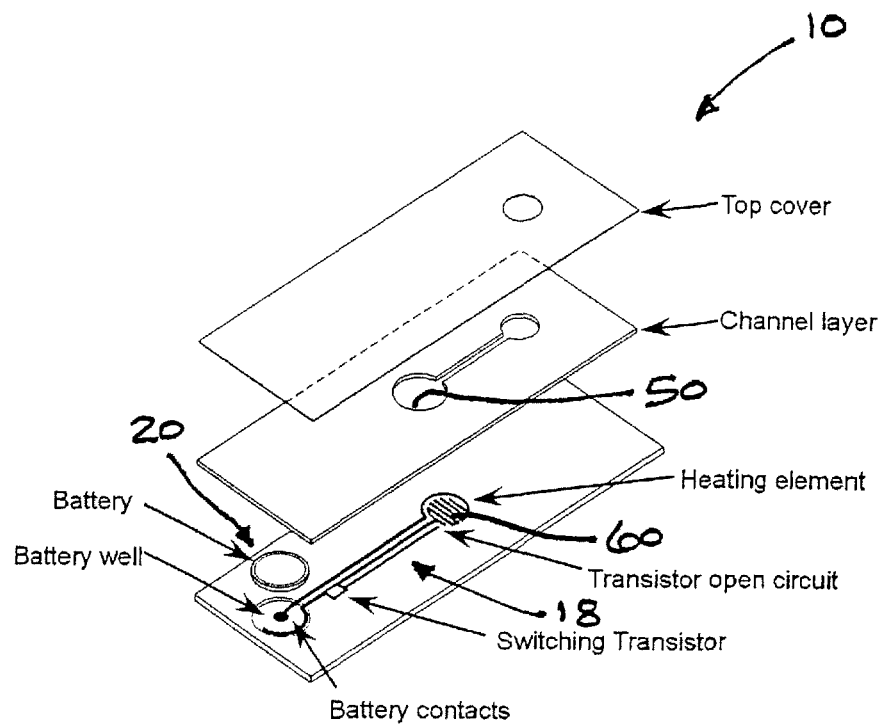
FIG. 13B is exploded perspective view of a disposable in-vitro diagnostic apparatus constructed in accordance with yet another aspect of the invention including the energy supply device of FIG. 13A.

FIG. 13B depicts an embodiment of the schematic in FIG. 13A in a disposable apparatus 10. The switching transistor provides the means to turn on and of the heating element, and when coupled with one of the thermally cycling devices describe prior, may also yield the thermal cycling profile.

What is claimed is:

1. A portable, disposable in-vitro diagnostic apparatus, comprising:
a body configured to be hand held, said body having a reaction medium supply chamber configured in selective fluid communication with a reaction chamber via a fluid conveying channel, said reaction chamber being beneath a sample reaction chamber, said reaction medium supply chamber containing a reaction fluid therein and said reaction chamber containing a thermal reaction medium therein, said reaction fluid being reactive with said thermal reaction medium to produce one of an endothermic or exothermic reaction beneath said sample reaction chamber.

2. The portable, disposable in-vitro diagnostic apparatus of claim 1 further comprising a conductive barrier separating said sample reaction chamber from said reaction chamber.

3. The portable, disposable in-vitro diagnostic apparatus of claim 2 further comprising an overflow chamber downstream from said reaction chamber.

4. The portable, disposable in-vitro diagnostic apparatus of claim 3 wherein said overflow chamber includes a hydrophobic membrane.

5. The portable, disposable in-vitro diagnostic apparatus of claim 1 further comprising a rupturable membrane selectively closing off said fluid conveying channel from said reaction medium supply chamber.

6. The portable, disposable in-vitro diagnostic apparatus of claim 5 wherein said fluid conveying channel includes a fluid wicking material contained therein.

7. The portable, disposable in-vitro diagnostic apparatus of claim 1 further including a self-actuatable valve disposed between said fluid conveying channel and said reaction chamber, said self-actuatable valve being movable between a closed position to close off said fluid conveying channel from said reaction chamber and an open position to allow fluid to flow from said fluid conveying channel into said reaction chamber.

8. The portable, disposable in-vitro diagnostic apparatus of claim 7 wherein said self-actuable valve moves between said open position and closed position in response to the endothermic or exothermic reaction.

9. The portable, disposable in-vitro diagnostic apparatus of claim 8 wherein said self-actuatable valve is a bimetallic material.

10. The portable, disposable in-vitro diagnostic apparatus of claim 8 wherein said self-actuatable valve is a heat memory alloy.

11. The portable, disposable in-vitro diagnostic apparatus of claim 1 wherein at least a portion of said thermal reaction medium is buffered.

12. The portable, disposable in-vitro diagnostic apparatus of claim 1 wherein said body is configured for electrical communication with an external power source.

* * * * *